US006391960B1

(12) United States Patent
Sambasivam et al.

(10) Patent No.: US 6,391,960 B1
(45) Date of Patent: *May 21, 2002

(54) MULTIPURPOSE HOT MELT ADHESIVE

(75) Inventors: Mahesh Sambasivam, Princeton; Charles W. Paul, Madison, both of NJ (US)

(73) Assignee: National Starch and Chemical Investment Holding Corporation, New Castle, DE (US)

(*) Notice: Subject to any disclaimer, the term of this patent is extended or adjusted under 35 U.S.C. 154(b) by 0 days.

This patent is subject to a terminal disclaimer.

(21) Appl. No.: 09/548,545

(22) Filed: Apr. 13, 2000

Related U.S. Application Data

(63) Continuation-in-part of application No. 09/219,938, filed on Dec. 23, 1998, now Pat. No. 6,232,391.

(51) Int. Cl.[7] .......... C08L 53/02; C08L 93/04; C08L 25/06; C08K 5/01
(52) U.S. Cl. .......... 524/505; 524/271; 524/274; 524/484; 525/98
(58) Field of Search .......... 524/271, 274, 524/505, 474; 525/98

(56) References Cited

U.S. PATENT DOCUMENTS

| | | | |
|---|---|---|---|
| 3,917,607 A | 11/1975 | Crossland et al. | 524/478 |
| 4,104,323 A * | 8/1978 | Hansen | 524/505 |
| 4,399,249 A | 8/1983 | Bildusas | 524/271 |
| 4,526,577 A | 7/1985 | Schmidt, Jr. et al. | 604/366 |
| 4,578,302 A | 3/1986 | Schmidt, Jr. et al. | 428/110 |
| 4,719,261 A | 1/1988 | Bunnelle et al. | 525/97 |
| 4,783,504 A * | 11/1988 | St. Clair | 524/271 |
| 4,944,993 A | 7/1990 | Raykovitz et al. | 428/290 |
| 5,024,667 A | 6/1991 | Malcolm et al. | 604/382 |
| 5,037,411 A | 8/1991 | Malcolm et al. | 604/358 |
| 5,057,571 A | 10/1991 | Malcolm et al. | 524/505 |
| 5,149,741 A | 9/1992 | Alper et al. | 525/95 |
| 5,290,842 A | 3/1994 | Sasaki et al. | 524/271 |
| 5,292,806 A * | 3/1994 | Diehl et al. | 525/98 |
| 5,331,038 A | 7/1994 | Dillman | 524/505 |
| 5,500,293 A * | 3/1996 | Lau et al. | 524/271 |
| 5,559,165 A | 9/1996 | Paul | 523/111 |
| 5,627,229 A | 5/1997 | Bunnelle et al. | 524/270 |
| 6,232,391 B1 * | 5/2001 | Sambasivam et al. | 524/505 |

FOREIGN PATENT DOCUMENTS

| | | | |
|---|---|---|---|
| EP | 0 358 900 A1 | 3/1990 | B32B/27/08 |
| EP | 0 368 102 A2 | 5/1990 | A61L/15/16 |
| EP | 0 368 141 A2 | 5/1990 | A61L/15/16 |
| EP | 0 472 942 A1 | 3/1992 | D04H/1/64 |
| EP | 0 532 831 | 4/1992 | C09J/153/00 |
| EP | 0 706 547 B1 | 4/1996 | C09J/153/02 |
| EP | 0 744 178 | 4/1996 | A61L/15/26 |
| EP | 0 802 251 | 4/1996 | C09J/153/02 |
| JP | 10088097 A | 4/1998 | C09J/153/00 |
| WO | WO 93/10734 | 6/1993 | A61F/13/58 |
| WO | WO 97/44404 | 11/1997 | C09J/153/02 |

* cited by examiner

*Primary Examiner*—Peter Szekely
(74) *Attorney, Agent, or Firm*—Cynthia L. Foulke

(57) ABSTRACT

A multipurpose hot melt adhesive comprising endblock resin in combination with a radial or linear SBS copolymer having a solution viscosity greater than 1000 cPs at 25% in toluene suitable for use as both a construction and elastic attachment adhesive in disposable products is disclosed.

12 Claims, No Drawings

MULTIPURPOSE HOT MELT ADHESIVE

This application is a continuation-in-part of prior application Ser. No. 09/219,938 filed on Dec. 23, 1998, now U.S. Pat. No. 6,232,391.

FIELD OF THE INVENTION

The present invention is directed to a multipurpose hot melt adhesive, which is suitable for use in disposable articles as both a construction and elastic attachment adhesive, comprising endblock resin in combination with a radial or linear styrene-butadiene-styrene or "SBS" block copolymer having a solution viscosity greater than 1000 cPs at 25% in toluene.

BACKGROUND OF THE INVENTION

In the production of disposable articles, hot melt adhesives are typically extruded at elevated temperatures (about 250° F. to 350° F.) directly onto a work piece, typically a polyethylene or polypropylene film, a nonwoven fabric, an absorbent material, a tissue, or a film which can then be bonded to another nonwoven fabric, absorbent material, tissue, or film using the hot melt adhesive. Application of the adhesive may be extruded by fine line, multi-dot, multi-line methods or spray techniques. The hot melt adhesive is used to laminate layers or attach elastic, particularly for waist or leg band closures for disposable diapers; elastic attachment also results in laminating.

Since in the assembly of disposable articles a variety of materials are bonded under a wide range of conditions, to optimize performance separate adhesives have evolved for use in the manufacture of disposable articles. This is particularly true in elastic attachment and in laminate construction. Construction requires an adhesive with controllable, relatively low viscosity, long open time, and sufficient bonding strength to maintain the mechanical integrity of the laminate. However, to bond elastic materials to substrates, a different adhesive which exhibits high creep resistance to ensure that the elastic, when under stress, does not move relative to the surfaces of the substrates or become partially or fully detached, is used.

The use of separate adhesives for laminate construction and for elastic attachment purposes, each having different formulas and properties, increases disposable article manufacturing complexity and can reduce productivity. Additionally, if multiple adhesives are required inventory and storage problems are increased. If the incorrect adhesive is used for elastic bonding it can lead to bond failure. Also, the applicator can become plugged. Such problems can lead to inferior products, lost production or both.

Accordingly a substantial need exists for a single adhesive having properties rendering the adhesive applicable to both lamination and elastic bonding applications. Such adhesives are known as multipurpose adhesives.

Construction adhesives are soft (tacky), have high peel strength, long open time and low cohesive strength. Elastic attachment adhesives are stiffer (not as tacky), high in cohesive strength, and shorter in open time, than construction adhesives. For multipurpose applications, in particular, elastic attachment, the balance of stiffness, cohesive strength, and open time is required for good performance.

Styrene-isoprene-styrene or "SIS" block copolymers are commonly used for elastic attachment in disposable products. SIS is chosen because, when compared to other block copolymers, for the same melt index and rubber content, SIS polymers provide a higher molecular weight and softer adhesive products. Adhesives used for elastic attachment need to contain high amounts of rubber and endblock resin to obtain adequate cohesion. For example, U.S. Pat. No. 5,149,741 to Alper discloses elastic attachment adhesives comprising 35 parts of SIS copolymer, in combination with 10 parts endblock resin.

As used herein, the "midblock" of the polymer refers to polymeric blocks which are substantially aliphatic. As will be discussed below, "midblock resin" refers to a tackifier which is compatible with the midblock of the polymer. "Endblock" of the polymer refers to polymeric blocks which are substantially aromatic. "Endblock resins", as will be discussed in detail below, are substantially aromatic and compatible with the endblock of the polymer.

At similar polymer content, melt index, and endblock resin level, a corresponding SBS-based adhesive is not as pressure sensitive as SIS due to high stiffness. The higher stiffness results from the lower entanglement molecular weight (higher entanglement density) of butadiene versus isoprene. U.S. Pat. No. 5,071,571 (Malcolm) discloses an adhesive for elastic attachment comprising low content of a very high molecular weight SBS copolymers.

Endblock resins are commonly used with SIS to improve cohesive strength in pressure sensitive adhesives. Endblock resins are not commonly used with SBS because it is difficult to ensure that the resin actually reaches the endblock due to the higher polarity of the butadiene midblock compared to isoprene midblock, which therefore tends to solubilize the endblock resin in the midblock to a large extent. In addition, endblock resins are not commonly used in SBS-based elastic attachment adhesives. U.S. Pat. No. 4,944,993 (Raykovitz) discloses low molecular weight, radial SBS polymers comprising a styrene content greater than 35% with endblock, and their use in construction and elastic attachment adhesives.

Endblock resins are effective only when they associate with the styrene portion of the block copolymer chain. Due to the closeness in solubility parameter of butadiene and styrene, the resin associates with the midblock or butadiene portion in low molecular weight SBS copolymers. However, in high molecular weight SBS copolymers, the longer butadiene chain does not favor this association to the same extent. This effect can be demonstrated by rheology curves, where the Tg of the butadiene block can be followed. For example, when 10 parts midblock resin are replaced by endblock resin, the midblock Tg should, in theory, decrease. The higher the midblock Tg after such a substitution, the more the endblock resin is in the midblock, instead of the endblock, of the rubber. By using a high molecular weight rubber at low levels, in combination with endblock resin, in accordance with the present invention, an adhesive with high cohesive strength can be attained due to the association of the endblock resin with the styrene block of the rubber. In addition, because lower amount of rubber is used, the stiffness is low and hence, the tack is high; for the same reason, open time is still high enough for multipurpose applications.

Therefore, unexpectedly, it has been found, in accordance with the present invention, that a multipurpose adhesive, for use in both elastic attachment and construction, can be prepared from a high molecular weight radial or linear SBS copolymer, without a high styrene content, and endblock resins. The adhesives of the present invention have both good cohesive strength (elastic attachment) and long open time and low stiffness, for good lamination bonds. The high molecular weight SBS copolymer allows use of a lower amount of the copolymer providing a softer, more pressure sensitive adhesive, with longer open time, when compared to use of a low molecular weight SBS copolymer. In addition, the presence of the endblock resin provides for a higher cohesion, at lower viscosity, when compared to adding more copolymer to the system to obtain the same increased level of cohesion.

The present invention is directed to hot melt adhesive compositions suitable for disposable constructions comprising an endblock resin and a high molecular weight styrene-butadiene block copolymer having a molecular weight such that at 25% in toluene, the viscosity is greater than 1000 cPs.

SUMMARY OF THE INVENTION

It has been found, in accordance with the present invention, that the use of endblock resin with high molecular weight rubber polymers provides a multipurpose hot melt adhesive which is suitable for use as both a construction and elastic attachment adhesive. Specifically, it has been found that a multiple-purpose adhesive having a high level of creep resistance, bond strength, and a low viscosity profile can be prepared comprising endblock resin in combination with a radial or linear SBS copolymer having a solution viscosity greater than 1000 cPs at 25% in toluene. The adhesive of the present invention will have a long open time, low stiffness, and good cohesive strength, all properties qualifying the adhesive as an effective multipurpose adhesive.

DESCRIPTION OF THE INVENTION

The present invention is directed to a multipurpose hot melt adhesive comprising: an SBS polymer with molecular weight such that at 25% in toluene, the viscosity is greater than 1000 cPs and an endblock resin.

The polymers useful in the hot melt adhesive of the present invention are block or multi-block copolymers having one of the following general configurations:

$(A-B)_n-A$ or $(AB)_n-X$ or $(A-B)_n$ wherein X is a multivalent coupling agent with functionality of two or more, and polymer blocks A are non-elastomeric polymer blocks and polymer blocks B are elastomeric polymer blocks of butadiene which has not been hydrogenated. Variable "n" is an integer equal to, or greater than, one. Copolymers useful in the present invention may be linear or radial. With radial copolymers, the functionality of X is three or more. Preferably the copolymer is linear. Some level of diblock copolymer, AB, may be present by design or due to incomplete coupling of the AB arms. Diblock is beneficial for increasing tack, peel and open time, but this must be counterbalanced with its effect of lowering cohesive strength. Diblock level will in general be below 50%, preferably less than 30%.

Examples of multivalent coupling agents, "X", include dibromoethane with functionality of 2; trisnonylphenyl phosphite and trichloromethylsilane, both with functionality of 3; and tetrachlorosilane with functionality of 4.

The non-elastomeric blocks A may comprise homopolymers or copolymers of vinyl monomers such as vinyl arenes, vinyl pyridines, vinyl halides and vinyl carboxylates, as well as acrylic monomers such as acrylonitrile, methacrylonitrile, esters of acrylic acids, etc. Monovinyl aromatic hydrocarbons include styrene, vinyl toluene, vinyl xylene, ethyl vinyl benzene as well as dicyclic monovinyl compounds such as vinyl naphthalene and the like. Other non-elastomeric polymer blocks may be derived from alpha olefins, alkylene oxides, acetals, urethanes, etc. Styrene is preferred, in an amount comprising less than 35 weight percent of the total copolymer composition, more preferably 25 to 32 weight percent, however it is most preferred that the least amount of styrene possible is used.

The elastomeric block component, B, making up the remainder of the copolymer is butadiene which has not been hydrogenated.

Most preferred for use herein are the linear A-B-A triblock copolymers where the elastomeric block is butadiene and the non-elastomeric block is styrene, and wherein the copolymer has a molecular weight such that its solution viscosity at 25% in toluene is greater than 1000 cPs, preferably greater than 2000, most preferably about 4000 cPs.

Typical of the rubbery block copolymers useful herein are the polystyrene-polybutadiene-polystyrene. Depending on the polymerization conditions, the polybutadiene midblock will contain different ratios of cis-1,4; trans-1,4; and 1,2 addition. Higher levels of 1,2 addition may be desirable to lower the viscosity for a given molecular weight. These copolymers may be prepared using methods familiar to one of ordinary skill in the art. Alternatively, these polymers may be obtained from Shell Chemical Co. under the tradenames Kraton D1101, with a styrene content of 31% and viscosity at 25% in toluene of 4000 cPs and Kraton D1184 with a styrene content of 30% and a viscosity at 25% in toluene of 20,000 cPs. Examples of other commercially available copolymers include SOLT 6302, 30% styrene, viscosity at 25% in toluene of 4000 cPs available from EniChem Americas (Agip USA Inc.); and DPX 563 with styrene content of 31% and viscosity in toluene at 25% of 7970 cPs available from Dexco.

Blends of these styrene containing copolymers with up to about 25%, preferably less than 10%, of other compatible non-functionalized block copolymers may also be employed. By the term "non-functionalized" is meant block copolymers which are not chemically modified so as to contain functional groups such as epoxy, anhydride, silane, sulfonate, amide or the like on the copolymer backbone. Useful compatible copolymers include those prepared using isoprene or butadiene elastomeric midblocks, whether hydrogenated or not, such as those available from Shell under the Kraton trademark. Particularly useful is that designated Kraton 1119.

While the optimum amounts of the copolymer used in the adhesive will vary depending on the end use application, the copolymer will generally be present in the adhesive formulation at a level less than 35%, generally greater than 5%, more often greater than 10%, and preferably about 15 to 20% by weight, most preferably about 18% by weight. Since the copolymer used in the hot melt adhesive of the present invention is of high molecular weight, only a small amount needs to be used, resulting in a long open time and soft product.

The hot melt adhesive compositions of the present invention also comprises a solid tackifier which is compatible with the midblock of the SBS copolymer. Representative resins include the $C_5/C_9$ hydrocarbon resins, synthetic polyterpenes, rosin, rosin esters, natural terpenes, and the like. More particularly, the useful tackifying resins include any compatible resins or mixtures thereof such as (1) natural and modified rosins including gum rosin, wood rosin, tall oil rosin, distilled rosin, hydrogenated rosin, dimerized rosin, and polymerized rosin; (2) glycerol and pentaerythritol esters of natural and modified rosins, including the glycerol ester of pale, wood rosin, the glycerol ester of hydrogenated rosin, the glycerol ester of polymerized rosin, the pentaerythritol ester of hydrogenated rosin, and the phenolic-modified pentaerythritol ester of rosin; (3) copolymers and terpolymers of natural terpenes, such as styrene/terpene and alpha methyl styrene/terpene; (4) polyterpene resins generally resulting from the polymerization of terepene hydrocarbons, such as the bicyclic monoterpene known as pinene, in the presence of Friedel-Crafts catalysts at moderately low temperatures; also included are the hydrogenated polyterpene resins; (5) phenolic modified terpene resins and hydrogenated derivatives thereof such, for example, as the resin product resulting from the condensation, in an acidic medium, of a bicyclic terpene and a phenol; (6) aliphatic petroleum hydrocarbon resins resulting from the polymerization of monomers consisting primarily of olefins and diolefins; also included are the hydrogenated aliphatic petroleum hydrocarbon resins; and (7) cyclic petroleum hydrocarbon resins and the hydrogenated derivatives thereof. Mixtures of two or more of the above described tackifying resins may be required for some formulations. Also included are the cyclic or acylic $C_5$ resins and aromatic modified acyclic or cyclic resins. Preferred is aromatic modified cyclic or acyclic $C_5$ resin.

A preferred tackifier is a $C_5/C_9$ hydrocarbon resin derived from petroleum with a Ring and Ball softening point between 100 to 105° C. The tackifiers, also referred to as "midblock resins", are generally present in the adhesive compositions in an amount greater than the amount of the block copolymer. Within this range, amounts of 30 to 70% by weight of the composition, preferably 50 to 65 weight percent are utilized.

The present invention also includes 2 to 30 weight percent of an endblock resin which is substantially aromatic. Examples of such endblock resins can be prepared from any substantially aromatic monomers having a polymerizable unsaturated group. Typical examples of such aromatic monomers include the styrenic monomers, styrene, alpha-methyl styrene, vinyl toluene, methoxy styrene, tertiary butyl styrene, chlorostyrene, etc., coumarone, indene monomers including indene, and methyl indene. The aromatic endblock resin is preferably present in amounts of 5 to 20 weight percent. Preferred is HERCOLITE 240 or KRISTALEX 5140, both of which are alpha methyl styrene resins available from Hercules, Inc.

The hot melt adhesive of the present invention also comprises 0 to 30, preferably 5 to 20, weight percent of an oil diluent. Suitable plasticizing or extending oils or liquid tackifiers include olefin oligomers and low molecular weight polymers as well as vegetable and animal oil and their derivatives. The petroleum derived oils which may be employed are relatively high boiling materials containing only a minor proportion of aromatic hydrocarbons (preferably less than 30%, more particularly, less than 15% by weight of the oil). Alternatively, the oil may be totally non-aromatic. Suitable oligomers include polypropylenes, polybutenes, hydrogenated polyisoprene, hydrogenated polybutadiene, or the like having average molecular weights between about 350 and about 10,000. Preferred are LUMINOL T350, a mineral oil available from Petrocanada and KAYDOL OIL available from Witco Corporation.

The hot melt adhesive of the present invention also comprises 0 to 3 weight percent, preferably, 0.3 to 3.0 weight percent, of an antioxidant. Among the applicable stabilizers or antioxidants included herein are the hindered phenols or hindered phenols in combination with a secondary antioxidant such as distearyl thiodipropionate ("DSTDP") or dilauryl thio-dipropionate ("DLTDP"). Hindered phenols as used herein are as phenolic compounds containing sterically bulky radicals in close proximity to the phenolic hydroxyl group thereof. The presence of these sterically bulky substituted radicals in the vicinity of the hydroxyl group serves to retard its stretching frequency and, correspondingly, the reactivity; this steric hindrance provides the phenolic compound with its stabilizing properties. Representative hindered phenols include: 1,3,5-trimethyl 2,4,6-tris (3,5-di-tert-butyl-4-hydroxybenzyl)benzene; pentaerythrityl tetrakis-3(3,5-di-tert-butyl-4-hydroxyphenyl) propionate; pentaerythritol tetrakis (3-lauryl thiodipropionate); n-octadecyl-3,5-di-tert-butyl-4-hydroxyphenol)-propionate; 4,4'-methylenebis (2,6-tert-butylphenol); 4,4'-thiobis (6-tert-butyl-o-cresol); 2,6-di-tertbutylphenol; 6-(4-hydroxyphenoxy)-2,4-bis(n-octyl-thio)-1,3,5-triazine; di-n-octadecyl 3,5-di-tert-butyl-4-hydroxy-benzyl-phosphonate; 2-(n-octylthio)ethyl 3,5-di-tert-butyl-4-hydroxy-benzoate; and sorbitol hexa[3-(3,5-di-tert-butyl-4-hydroxyphenyl)-propionate]. Preferred antioxidants are SUMILIZER TDP, a secondary antioxidant available from Sumitomo Chemical Company and IRGANOX 1010 a hindered phenol primary antioxidant available from Ciba-Geigy. The stabilizer is present in amounts of 0.3 to 3% by weight, preferably 0.3 to 1.5%, most preferably 0.8%.

Optional additives may be incorporated into the hot melt compositions depending on the end use of the composition. Among these additives may be included colorants such as titanium dioxide; and fillers such as talc and clay, etc., as well as minor amounts (e.g., less than about 5%) of a petroleum derived wax.

One embodiment of the present invention is a multipurpose hot melt adhesive comprising:

(a) 5 to than 35 weight percent of a styrene-butadiene-styrene block copolymer with molecular weight such that at 25% in toluene the viscosity is greater than 1000 cPs;

(b) 2 to 30 weight percent endblock resin prepared from any substantially aromatic monomers having a polymerizable unsaturated group;

(c) 30 to 70 weight percent of a solid tackifier;

(d) 0 to 25% of a compatible non-functionalized block copolymer;

(e) 0 to 30 weight percent oil; and (e) 0 to 3 weight percent antioxidant wherein the tackifier is present in an amount greater than the block copolymer and wherein the adhesive has a viscosity less than 35,000 cPs at 325° F. and a cohesive strength measured in Hang-Bead time of greater than 45 seconds.

In another embodiment the adhesive comprises:

(a) 5 to than 35, preferably 10 to 35, weight percent of a styrene-butadiene-styrene block copolymer with molecular weight such that at 25% in toluene the viscosity is greater than 2000 cPs, and less than 32% styrene;

(b) 2 to 30 weight percent of the endblock resin;

(c) 30 to 70 weight percent of a solid tackifier;

(d) 0 to 30 weight percent oil; and (e) 0 to 3 weight percent antioxidant wherein the tackifier is present in an amount greater than the block copolymer and wherein the adhesive has a viscosity less than 35,000 cPs at 325° F. and a cohesive strength measured in Hang-Bead time of greater than 45 seconds.

In a further embodiment the adhesive comprises:
(a) 10 to 25 weight percent of a styrene-butadiene-styrene block copolymer with molecular weight such that at 25% in toluene the viscosity is greater than 2000 cPs, and less than 32 weight percent styrene;
(b) 5 to 20 weight percent endblock resin;
(c) 45 to 65 weight percent of a tackifier;
(d) 0 to 30 weight percent oil; and
(e) 0 to 3 weight percent antioxidant.

In a preferred embodiment, the present invention is directed to a multipurpose hot melt adhesive comprising:
(a) 15 to 20 weight percent of a styrene-butadiene-styrene block copolymer with molecular weight such that at 25% in toluene the viscosity is greater than 2000 cPs and 32 weight percent styrene;
(b) 5 to 20 weight percent aromatic resin;
(c) 45 to 65 weight percent of a solid tackifier;
(d) 5 to 20 weight percent oil; and
(e) 0.3 to 1.5 weight percent antioxidant wherein the tackifier is present in an amount greater than the block copolymer and wherein the adhesive has a viscosity less than 35,000 cPs at 325° F. and a cohesive strength measured in Hang-Bead time of greater than 45 seconds.

The resultant adhesives may be used in the assembly or construction of various disposable articles including, but not limited to, disposable diapers, disposable feminine products, adult incontinent products, hospital gowns, bed pads and the like. In particular, adhesives are useful for the assembly of disposable articles wherein at least one polyethylene or polypropylene substrate is bonded to at least one tissue, nonwoven, polyethylene or polypropylene substrate. In addition, the adhesives are useful in the bonding of elastic to polyethylene, polypropylene or nonwoven substrate so as, for example, to impart elongation resistant gathers thereto. The adhesive may also be utilized in less demanding disposable construction applications such as for end or perimeter sealing.

The use of high molecular weight copolymers allows the use of a smaller amount of polymer, resulting in a less stiff adhesive formulation desirable for a pressure sensitive adhesive. The adhesive of the present invention will have a stiffness less than $15 \times 10^5$ dyne/cm$^2$ at 40° C., preferably less than $10 \times 10^5$ dyne/cm$^2$ at 40° C.

Low stiffness, combined with high loss modulus, leads to high loop tack. Loop tack is a measure of an adhesive's grab. High loop tack indicates that the adhesive will form a good pressure sensitive bond with low applied pressure. A pressure sensitive hot melt adhesives, in accordance with the present invention, will display loop tack values preferably greater than 50 oz/in$^2$, most preferably 90–200 oz/in$^2$.

The viscosity of the resulting adhesive formulation will be less than 35,000 cPs at 325° F., allowing for use with most conventional adhesive application machinery. In a more preferred embodiment, the viscosity of the adhesive formulation of the present invention will be less than 15,000 cPs, providing the adhesive with sprayability and processability.

A preferred composition for a hot melt adhesive in accordance with the present invention, which is sprayable and suitable for elastic attachment, will have a viscosity less than 35,000 cPs at 325° F. and a cohesive strength measured in Hang-Bead time of greater than 45 seconds, and preferably the SBS block copolymer comprises less than 35% styrene.

A preferred composition for a multipurpose adhesive in accordance with the present invention, will have a viscosity less than 35,000 cPs at 325° F., a cohesive strength measured in Hang-Bead time of greater than 45 seconds, a loop tack greater than 50 oz/in$^2$, a stiffness less than $15 \times 10^5$ dyne/cm$^2$ at 40° C., and preferably the SBS block copolymer comprises less than 35% styrene.

The adhesive formulations of the present invention, in addition to being suitable for elastic attachment, have a long open time and high pressure sensitivity allowing them to be very good as a construction adhesive. In addition, the adhesive of the present invention will have good cohesive strength as measured by Hang-Bead time. Hang-Bead time is a relative measure of cohesive strength; the adhesives of the present invention will have a Hang-Bead time of at least 45 seconds, preferably greater than 150 seconds, or most preferably greater than 500 seconds.

The following examples are merely illustrative and not intended to limit the scope of the present claims in any manner.

EXAMPLES

The adhesives of the invention were prepared using the following procedure:

In a sigma blade mixer, heated to about 163° C., the rubber was charged along with the antioxidants, tackifying resin and mineral oil. The rubber to plasticizer ratio (oil+resin) was about 1:1.5. Mixing of the contents was continued until a homogeneous mixture was obtained. At this point, the remainder of the resin was added slowly followed by addition of the remainder of the mineral oil. Mixing was then continued for about 10 more minutes. The molten adhesive was then poured into a silicone release-coated container and allowed to cool to room temperature.

The following copolymers were used:

| Rubber | *Solution Viscosity, Styrene Diblock | % | % | Structure |
|---|---|---|---|---|
| Sol T 6414 | 350 | 40 | 25 | Branched |
| Sol T 6302 | 4,000 | 31 | 10 | Linear |
| D1184 | 20,000 | 31 | 16 | Branched |
| DPX 563 | 7970 | 31 | 0 | Linear |
| D1122X | 730 | 38 | 10 | Branched |

*Neat polymer concentration, 25% w in Toluene @ 73° F.

Sol T 6414 is available from EniChem Americas (Agip USA Inc.) and D1122X is available from Shell Chemical Company.

The following tests were performed on the adhesives to determine the viscosity, cohesive strength, peel strength, tack, and stiffness:

Viscosity

Viscosity measurements were made in a Brookefield viscometer at 325° F. and are shown in cPs units.

Cohesive Strength Measurements

It is generally recognized that to hold the elastics in place in disposable articles, an adhesive with a high resistance to creep under the stress of the elastic, or high "cohesive strength," is required. Various measures of cohesive strength have been used in the past. Here, cohesive strength was measured using a creep test on a single bead of adhesive. The bead is applied to a plate at 0.53 grams/meter. The plate contains a slit cut transverse to the direction in which the bead is applied. Each slit is 1/8" wide and extends to one side of the plate. The bead of adhesive is applied to the plate and bridges over the slit, such that it does not droop into the slit itself. The plate is then placed in an oven at 105° F. and allowed to equilibrate for 20 min. A 40 gram weight attached to a paper clip is then hung on the bead of adhesive in the section over the slit using the other end of the paper clip (size #1 GEM CLIPS available form BT Office Products International). The time required for the adhesive bead to break is termed the "Hang-Bead time".

Peel Strength Measurements

Peel strength was measured by performing a 180° peel test on high density polyethylene, "HDPE", substrate using an Instron. About 2 to 3 mil thick coating of the adhesive is applied on to Mylar film using heated rollers and bonded to silicone coated release paper. Three specimens each 3"×1" in dimensions are cut perpendicular to the machine direction from the coated Mylar. After conditioning overnight at 72° F. and 50% relative humidity, the release paper is removed and the specimens are bonded to a HDPE plate. The bonds are then rolled using a 4.5 lb roller. After conditioning the bonds for about half-hour, they are peeled in the Instron at 2"/minute. The HDPE plate is in the stationary jaw, and the Mylar is in the movable jaw. The results are reported as an average load in grams.

Loop Tack Measurements

Loop tack is measured using the TMI Loop Tack tester made by cutting 5"×1" dimensions specimens of the Mylar coated laminates along the machine direction. After conditioning overnight at 72° F. and 50% relative humidity, the laminate is folded into a loop by taping the ends together. The loop is then mounted on the Loop tack tester and a stainless steel plate is clamped to the base of the tester. When the test is started, the loop is brought in contact with the Stainless Steel plate and then withdrawn. The load it takes to withdraw from the plate is recorded as the loop tack in oz/in$^2$.

Rheology Study

A Rheometrics Dynamic Mechanical Analyzer (model RDA 700) was used to obtain the elastic (G') and loss (G") moduli versus temperature. The instrument was controlled by Rhios software version 4.3.2. Parallel plates 8 mm in diameter and separated by a gap of about 2 mm were used. The sample was loaded and then cooled to about −100° C. and the time program started. The program test increased the temperature at 5° C. intervals followed by a soak time at each temperature of 10 seconds. The convection oven containing the sample was flushed continuously with nitrogen. The frequency was maintained at 10 rad/s. The initial strain at the start of the test was 0.05% (at the outer edge of the plates.) An autostrain option in the software was used to maintain an accurately measurable torque throughout the test. The option was configured such that the maximum applied strain allowed by the software was 80%. The autostrain program adjusted the strain at each temperature increment if warranted using the following procedure. If the torque was below 200 g-cm, the strain was increased by 25% of the current value. If the torque was above 1200, it was decreased by 25% of the current value. At torques between 200 and 1200 g-cm, no change in strain was made at that temperature increment. The shear storage or elastic modulus (G') and the shear loss modulus (G") are calculated by the software from the torque and strain data. Their ratio, G"/G', also known as the tan delta, was also calculated. The temperature corresponding to the tan δ peak associated with the midblock is reported as the midblock Tg.

In the following tables, stiffness values, G', are reported in units of $10^5$ dyne/cm$^2$ at 40° C.

Open Time Measurements

Open time of the adhesives was measured by bonding polyethylene to polyethylene in a Kanebo bond tester. A known amount of adhesive at 350° F. is applied as a bead on a polyethylene film mounted on a plate. The open time is adjusted in the bond tester to any desired value. After the open time elapses, the tester bonds another sheet of polyethylene, mounted on a plate, on to the adhesive bead under a constant load. The bead width is measured as a function of open time. The open time of the adhesive is taken as the time when the bead width changes from greater than or equal to 2 mm to less than 2 mm.

Example 1

Table I shows the effect of endblock resins on the cohesive strength of the adhesives. Samples I-1, I-2, I-3, I-4 were prepared using the general mixing procedure described earlier using 18 weight percent SOLT 6302 and 16 weight percent oil in Sample I-1 and 18 weight percent oil in Samples I-2, I-3 and I-4. In each sample, the tackifier used is a $C_5/C_9$ hydrocarbon resin derived from petroleum with a Ring and Ball of 100 to 105° C.

It can be seen that the cohesive strength (Hang-Bead time) of Sample 1, which does not contain endblock, is significantly lower than Samples I-2, I-3, I-4 due to the absence of endblock resin. The cohesive strength is also dependent on the amount of endblock resin added. This is evident in Samples I-2, I-3, I-4, which show an increase in cohesive strength with increasing amount of endblock resin. In multipurpose applications, which includes both elastic attachment and construction, it is desirable to have high peel and cohesive strengths with considerable tack or pressure sensitivity. It is well known that it is difficult to optimize cohesive and peel strengths without altering one or the other. Sample I-4 in Table I has high cohesive strength but very low peel strength. In addition, the sacrifice for this high cohesive strength of Sample I-4 is the high stiffness and very low tack. While Sample I-4 may be suitable for some elastic applications, it would make a poor construction adhesive due to its lack of pressure sensitivity.

TABLE I

| Resin | | Amt. (wt. %) | Visc. @ 325° F. (cPs) | Hang-Bead time (s.) | Peel (g.) | Tack (oz/in$^2$) | Stiffness @ 40° C. ($10^5$ dyne/cm$^2$) |
|---|---|---|---|---|---|---|---|
| I-1 | Tackifier | 66 | 8,450 | 117 | 2582 | 191 | 3.0 |
| | Hercolite 240 | 0 | | | | | |

TABLE I-continued

| Resin | | Amt. (wt. %) | Visc. @ 325° F. (cPs) | Hang-Bead time (s.) | Peel Tack (g.) | Stiffness @ 40° C. | |
|---|---|---|---|---|---|---|---|
| | | | | | | (oz/in$^2$) | ($10^5$ dyne/cm$^2$) |
| I-2 | Tackifier | 54 | 10,050 | 910 | 1876 | 101 | 3.8 |
| | Hercolite 240 | 10 | | | | | |
| I-3 | Tackifier | 49 | 10,700 | 1074 | 1129 | 78 | 5.5 |
| | Hercolite 240 | 15 | | | | | |
| I-4 | Tackifier | 44 | 14,700 | 2310 | 625 | 3 | 40 |
| | Hercolite 240 | 20 | | | | | |

Example 2

Table II demonstrates that different high molecular weight rubbers can be used to achieve a balance between cohesive strength and peel strength. Each sample was prepared with 18 weight percent rubber; 54 weight percent of the tackifier used in Example I; 10 weight percent Hercolite 240; and 18 weight percent oil.

TABLE II

| | Polymer | Visc. @ 325° F. (cPs) | Hang-Bead (s.) | Peel (g.) | Tack (oz/in$^2$) | Stiffness @ 40° C. ($10^5$ dyne/cm$^2$) |
|---|---|---|---|---|---|---|
| II-1 | Sol T 6302 | 10,050 | 910 | 1876 | 101 | 3.8 |
| II-2 | DPX 563 | 13,920 | 784 | 1780 | 111 | 3.4 |
| II-3 | D1184 | 26,050 | 3,050 | 1476 | 108 | 2.9 |

The $C_5/C_9$ resin used in Samples III-1 and III-4 are a $C_5/C_9$ hydrocarbon resin derived from petroleum with a Ring and Ball softening point between 100–105° C. UnitacR100L is a pentaerythritol ester of rosin available from Union Camp. Zonatac 105 is a styrenated terpene available from Arizona Chemical Company.

TABLE III

| | Polymer | Amt. (wt. %) | Resin | Amt (wt. %) | Oil (wt. %) | Visc. @ 325° F. (cPs) | Hang-bead time (s.) | Peel (g.) | Tack (oz/in$^2$) | Stiffness @ 40° C. ($10^5$dyne/cm$^2$) |
|---|---|---|---|---|---|---|---|---|---|---|
| III-1 | D1122 | 15 | $C_5/C_9$ resin | 52 | 25 | 835 | 11 | 868 | 96 | 2.7 |
| | | | Kristalex 5140 | 8 | | | | | | |
| III-2 | D1184 | 10.64 | Unitac R100L | 53.3 | 19.6* | 1400 | 0 | 2026 | 49 | 0.9 |
| | | | Zonatac 105 | 15.96 | | | | | | |
| III-3 | D1184 | 10.64 | Unitac R100L | 43.3 | 19.6* | 1,950 | 27 | 2260 | 8 | 1.7 |
| | | | Zonatac 105 | 15.96 | | | | | | |
| | | | Hercolite 240 | 10.0 | | | | | | |
| III-4 | Sol T 6302 | 18 | $C_5/C_9$ resin | 54 | 18 | 10,050 | 910 | 1876 | 101 | 3.8 |
| | | | Hercolite 240 | 10 | | | | | | |

Example 3

Table III compares samples made from prior art to that of the present invention. Sample III-1 is made using the example in Raykovitz, U.S. Pat. No. 4,944,993. Sample III-2 is made using the preferred example of Malcolm, EP 0 368 141 A2. Samples III-1 and III-2 have very poor cohesive strength compared to Sample III-4 corresponding to the present invention. Sample III-3 shows that by adding endblock resin to the preferred example of Malcolm's patent, it is possible to improve the cohesive strength. Although Raykovitz patent example contains endblock resin, it does not demonstrate the effect of endblock resin on cohesive strength and peel strength. This invention clearly demonstrates the effective use of endblock resins in combination with high molecular weight rubbers to optimize peel and cohesive strengths.

Example 4

The glass transition temperature, Tg, of the midblock (butadiene in this application) is an important parameter, which determines the stiffness and the peel strength of the adhesive at room temperature. In addition, it can be used to study the effect of endblock resins in hot melt adhesives. When the midblock resin is replaced in part by the endblock resin, the Tg of the midblock is expected to decrease, provided the endblock does not have any association with the midblock. Also, the benefit of adding an endblock is achieved only when it associates with the endblock of the block copolymer rubber. In SBS rubbers, due to the closeness in solubility parameters of styrene and butadiene, which are about 8.9 and 8.4, respectively, the endblock resins tend to associate with the midblock too. This association is readily seen as an increase in midblock Tg on adding the endblock resin. The extent of this association is dependent on the molecular weight of the rubber and the softening point of the endblock resin.

Table IV compares the midblock Tg in low molecular weight and high molecular weight SBS rubber formulations. Samples IV-1 and IV-2 were prepared according to Raykovitz, U.S. Pat. No. 4,944,993. In each of the samples in Table IV, the tackifier is a $C_5/C_9$ hydrocarbon resin derived from petroleum with a Ring and Ball softening point between 100 to 105° C.

Sample IV-4 is an example of the present invention. It can be seen that the increase in midblock Tg on adding endblock resin is much higher in a low molecular weight SBS, Sol T 6414 (Sample IV-2), than in a high molecular weight SBS, Sol T 6302 (Sample IV-4). The consequence of this greater association with the midblock in Sol T 6414 can be readily seen in the cohesive strength. The cohesive strength increase on adding endblock resin, is much lower in Sol T 6414 (Sample IV-2) than in Sol T 6302 (Sample IV-4). Hence, by using a high molecular weight rubber in combination with endblock resin, it is possible to achieve high cohesive strength at low levels of rubber.

TABLE IV

| Sample | Polymer | Amt. (wt. %) | Resin | Amt. (wt. %) | Oil (wt. %) | Midblock Tg (° C.) | ΔTg (° C.) | Hang-Bead time, (s.) |
|---|---|---|---|---|---|---|---|---|
| IV-1 | Sol T 6414 | 30 | tackifier | 59 | 11 | 20 | — | 310 |
|  |  |  | Hercolite 240 | 0 |  |  |  |  |
| IV-2 | Sol T 6414 | 30 | tackifier | 49 | 11 | 27 | 7 | 537 |
|  |  |  | Hercolite 240 | 10 |  |  |  |  |
| IV-3 | Sol T 6302 | 18 | tackifier | 66 | 16 | 19 | — | 117 |
|  |  |  | Hercolite 240 | 0 |  |  |  |  |
| IV-4 | Sol T 6302 | 18 | tackifier | 56 | 16 | 21 | 2.0 | 943 |
|  |  |  | Hercolite 240 | 10 |  |  |  |  |

Example 5

In hot melt adhesives applications, it is desirable to have long open time. Open time of the adhesive can be broadly defined as the longest time one can wait after applying the adhesive before bonding and still obtain an acceptable bond. Table V compares the adhesive of present invention (Sample V-2) to an adhesive prepared according to Raykovitz, U.S. Pat. No. 4,944,993, with higher amount of rubber (Sample V-1). The higher amount of rubber in Sample V-1 is to achieve sufficient cohesive strength. It can be seen that the open time in Sample V-1 is much lower than that of Sample V-2. The longer open time is another benefit of adding lower amounts of high molecular weight rubber while maintaining good cohesive strength.

In each of the samples in Table V, the tackifier is a $C_5/C_9$ hydrocarbon resin derived from petroleum with a Ring and Ball softening point between 100 to 105° C.

What is claimed is:

1. A hot melt adhesive comprising:
(a) 5 to 35 weight percent of a styrene-butadiene-styrene block copolymer with molecular weight such that at 25% in toluene the viscosity is greater than 1000 cPs wherein the styrene-butadiene-styrene block copolymer comprises less than 35% styrene;
(b) 2 to 30 weight percent endblock resin prepared from any substantially aromatic monomers having a polymerizable unsaturated group;
(c) 30 to 70 weight percent of a solid tackifier;
(d) 0 to 25% of a compatible non-functionalized block copolymer;
(e) 0 to 30 weight percent oil; and
(f) 0 to 3 weight percent antioxidant wherein the tackifier is present in an amount greater than the block copolymer and wherein the adhesive has a viscosity less than 35,000 cPs at 325° F. and a cohesive strength measured in Hang-Bead time of greater than 45 seconds.

2. A hot melt adhesive consisting essentially of:
(a) 5 to 35 weight percent of a styrene-butadiene-styrene block copolymer with molecular weight such that at 25% in toluene the viscosity is greater than 1000 cPs wherein the styrene-butadiene-styrene block copolymer comprises less than 35% styrene;
(b) 2 to 30 weight percent endblock resin prepared from any substantially aromatic monomers having a polymerizable unsaturated group;
(c) 30 to 70 weight percent of a solid tackifier;
(d) 0 to 25% of a compatible non-functionalized block copolymer;
(e) 0 to 30 weight percent oil; and
(f) 0 to 3 weight percent antioxidant wherein the tackifier is present in an amount greater than the block copolymer and wherein the adhesive has a viscosity less than 35,000 cPs at 325° F. and a cohesive strength measured in Hang-Bead time of greater than 45 seconds.

3. The hot melt adhesive according to claim 1 wherein the adhesive has a loop tack greater than 50 oz/in² and a stiffness less than $15 \times 10^5$ dyne/cm² at 40° C.

4. The hot melt adhesive of claim 1 wherein the endblock resin is selected from the group consisting of styrene, alphamethyl styrene, vinyl toluene, methoxy styrene, ter-

TABLE V

| Sample | Polymer | Amt. (wt. %) | Resin | Amount (wt. %) | Oil (wt. %) | Visc. @ 325° C. (cPs) | Open time, (s.) | Hang-bead time, (s.) |
|---|---|---|---|---|---|---|---|---|
| V-1 | D1122X | 30 | tackifier | 59 | 11 | 10,650 | 1.0 | 517 |
| V-2 | Sol T 6302 | 18 | tackifier | 54 | 18 | 10,050 | 2.0 | 917 |
|  |  |  | Hercolite 240 | 10 |  |  |  |  | tiary butyl styrene, chlorostyrene, coumarone, indene, and methyl indene.

5. A hot melt adhesive consisting essentially of:
   (a) 5 to 35 weight percent of a styrene-butadiene-styrene block copolymer with molecular weight such that at 25% in toluene the viscosity is greater than 2000 cPs, and wherein the styrene-butadiene-styrene block copolymer comprises less than 32% styrene;
   (b) 2 to 30 weight percent endblock resin prepared from any substantially aromatic monomers having a polymerizable unsaturated group;
   (c) 30 to 70 weight percent of a solid tackifier;
   (d) 0 to 25% of a compatible non-functionalized block copolymer;
   (e) 0 to 30 weight percent oil; and
   (f) 0 to 3 weight percent antioxidant; wherein the tackifier is present in an amount greater than the copolymer and wherein the adhesive has a viscosity less than 35,000 cPs at 325° F. and a cohesive strength measured in Hang-Bead time of greater than 45 seconds.

6. A hot melt adhesive according to claim 3 wherein the adhesive has a loop tack greater than 50 oz/in$^2$ and a stiffness less than $15 \times 10^5$ dyne/cm$^2$ at 40° C.

7. A hot melt adhesive consisting essentially of:
   (a) 10 to 25 weight percent of a styrene-butadiene-styrene block copolymer with molecular weight such that at 25% in toluene the viscosity is greater than 2000 cPs, and comprises less than 32 weight % styrene;
   (b) 5 to 20 weight percent endblock resin prepared from any substantially aromatic monomers having a polymerizable unsaturated group;
   (c) 45 to 65 weight percent of a solid tackifier;
   (d) 0 to 25% of a compatible non-functionalized block copolymer;
   (e) 0 to 30 weight percent oil; and
   (f) 0 to 3 weight percent antioxidant
wherein the adhesive has a viscosity less than 35,000 cPs at 325° F. and a cohesive strength measured in Hang-Bead time of greater than 45 seconds.

8. A hot melt adhesive according to claim 5 wherein the adhesive has a loop tack greater than 50 oz/in$^2$ and a stiffness less than $15 \times 10^5$ dyne/cm$^2$ at 40° C.

9. A hot melt adhesive consisting essentially of:
   (a) 15 to 20 weight percent of a styrene-butadiene-styrene block copolymer with molecular weight such that at 25% in toluene the viscosity is greater than 2000 cPs, and comprises less than 32% styrene;
   (b) 5 to 20 weight percent endblock resin prepared from any substantially aromatic monomers having a polymerizable unsaturated group;
   (c) 45 to 65 weight percent of a solid tackifier;
   (d) 0 to 25% of a compatible non-functionalized block copolymer;
   (e) 5 to 20 weight percent oil; and
   (f) 0.3 to 1.5 weight percent antioxidant
wherein the adhesive has a viscosity less than 35,000 cPs at 325° F. and a cohesive strength measured in Hang-Bead time of greater than 45 seconds.

10. A hot melt adhesive according to claim 7 wherein the adhesive has a loop tack greater than 50 oz/in$^2$ and a stiffness less than $15 \times 10^5$ dyne/cm$^2$ at 40° C.

11. A disposable product bonded utilizing the hot melt adhesive composition of claim 1.

12. A disposable product comprising a hot melt adhesive bonded utilizing the hot melt adhesive composition of claim 2.

* * * * *